United States Patent [19]
Kim et al.

[11] Patent Number: 5,672,789
[45] Date of Patent: Sep. 30, 1997

[54] CATALYST FOR FLUORINATION OF 1,1-DICHLORO-1-FLUOROETHANE AND PROCESS FOR THE PREPARATION OF 1,1,1-TRIFLUOROETHANE USING THE SAME

[75] Inventors: Hoon Sik Kim; Byung Gwon Lee; Honggon Kim; Hyunjoo Lee, all of Seoul, Rep. of Korea

[73] Assignee: Korea Institute of Science and Technology, Seoul, Rep. of Korea

[21] Appl. No.: 623,105

[22] Filed: Mar. 28, 1996

[30] Foreign Application Priority Data

Mar. 28, 1995 [KR] Rep. of Korea .................. 6718/1995

[51] Int. Cl.$^6$ .................................................. C07C 17/08
[52] U.S. Cl. ............................................................ 570/168
[58] Field of Search ........................................ 570/168

[56] References Cited

U.S. PATENT DOCUMENTS

| 4,547,483 | 10/1985 | Müller et al. | 570/168 |
| 5,407,877 | 4/1995 | Scott | 570/168 |
| 5,453,551 | 9/1995 | Lacroix et al. | 570/168 |
| 5,545,774 | 8/1996 | Rao | 570/168 |

Primary Examiner—Alan Siegel
Attorney, Agent, or Firm—Darby & Darby

[57] ABSTRACT

A catalyst for fluorination of 1,1-dichloro-1-fluoroethane which is obtained by mixing chromic hydroxide and an aqueous solution of magnesium chloride, reacting the mixture with an aqueous solution of HF and then calcining the resulting product and a process for preparing 1,1,1,-trifluoroethane by reacting 1,1-dichloro-1-fluoroethane with HF in the presence of the above catalyst are provided.

5 Claims, No Drawings

CATALYST FOR FLUORINATION OF 1,1-DICHLORO-1-FLUOROETHANE AND PROCESS FOR THE PREPARATION OF 1,1,1-TRIFLUOROETHANE USING THE SAME

BACKGROUND OF THE INVENTION

1. Field of the Invention

The present invention relates to a catalyst effective for synthesizing 1,1,1-trifluoroethane ($CF_3CH_3$: hereinafter referred to simply as HFC-143a) from 1,1-dichloro-1-fluoroethane ($CCl_2FCH_3$: hereinafter referred to as HCFC-141b) and hydrogen fluoride (hereinafter referred to as HF) and a process for preparing HFC-143a. More particularly, the present invention relates to a catalyst effective for preparing HFC-143a, which comprises Cr and Mg in an appropriate ratio and is obtained by the steps of mixing chromic hydroxide ($Cr(OH)_3.H_2$) with an aqueous solution of magnesium chloride and reacting the mixture with HF and then calcining the resulting product. The present invention also relates to a process for preparing HFC-143a from HCFC-141b and HF with high selectivity and high yield in the presence of the aforementioned catalyst.

2. Description of the Prior Art

CFC (chlorofluorocarbon) has been widely used in various industrial fields due to its non-toxicity to humans and its good physico-chemical properties. However, it has been revealed that CFC is a primary factor in destroying the ozone layer in the stratosphere. Therefore, its production and use has been restricted under international agreement by Montreal Protocol since 1987. Therefore, it has been intensively investigated to develop materials which can be substituted for these CFC compounds and it has been known that HFC-143a is one of the promising CFC substitutes. HFC-143a can be used alone or in combination with HFC-143a ($CF_3CH_2F$) or HFC-125 ($CF_3CHF_2$) as a coolant. HFC-143a is anticipated to be an excellent substitute for the conventional R-502 (azeotropic mixture of HCFC-22 and CFC-115).

HFC-143a can be prepared by reacting HCFC-141b with HF as shown in the following reactions:

$$CCl_2FCH_3 + HF \longrightarrow CClF_2CH_3 + HCl$$
(HCFC-141b) (HCFC-142b)

$$CClF_2CH_3 + HF \longrightarrow CF_3CH_3 + HCl$$
(HCFC-142b) (HFC-143a)

Namely, HFC-143a can be prepared by substituting the chlorine of HCFC-141b molecule with the fluorine and for effective substitution, the presence of an appropriate catalyst is essentially required.

Several processes for preparing HFC-143a are disclosed in Japanese Patent Publication (B) 59-46211, Japanese Laid-Open Patent Publication (A) 3-151335 and U.S. Pat. No. 4,091,043. But most of these processes are for the production of HCFC-142b. and therefore, the yield of HFC-143a is not satisfactory.

Japanese Patent Publication (B) 59-46211 and U.S. Pat. No. 4,091,043 disclose a process for simultaneously preparing HCFC-142b and HFC-143a by reacting 1,1,1-trichloroethane ($CCl_3CH_3$) with HF in the liquid phase in the presence of $SbCl_5$ catalyst. However, the selectivity of HFC-143a among the reaction products is at most 80% in the aforementioned process and thus, in case the main object is to obtain HFC-143a, the method is not effective. Moreover, if the reaction temperature is raised to enhance the conversion of the starting materials, the excessive production of by-products becomes a significant problem. Japanese Laid-Open Patent Publication (A) 3-151335 discloses that the catalyst comprising $SbCl_3$ and $SbCl_5$ in an appropriate ratio is especially preferable in preparing HCFC-142b. When this catalyst is used, it is descried that the conversion of the raw material is 94–99%. As shown above, the liquid phase process using Sb-catalyst appears to be effective in the preparation of HCFC-142b but not appropriate for the production of HFC-143a.

SUMMARY OF THE INVENTION

Therefore, an object of the present invention is to provide a novel heterogeneous catalyst for efficient gas-phase production of HFC-143a from HCFC-141b, which comprises Cr and Mg in an appropriate ratio.

Another object of the present invention is to produce HFC-143a using the aforementioned catalyst.

The present inventors have intensively studied to provide an effective catalyst system for the production of only HFC-143a and found that a catalyst obtained by mixing chromic hydroxide ($Cr(OH)_3.H_2O$) and an aqueous solution of magnesium chloride, reacting the mixture with an aqueous solution of HF and then calcining the resulting product is suitable for such purposes. This catalyst has an excellent activity in fluorination of HFC-141b and appears to be particularly suitable in the preparation of HFC-143a as evidenced by the fact that it causes no other by-product than HFC-143a and shows no loss of its activity after several months of use thereof.

DETAILED DESCRIPTION OF THE INVENTION

The catalyst according to the present invention contains Cr and Mg in the weight ratio of 1:0.2 to 1:10, preferably 1:0.3 to 1:4. The suitable fluorination reaction temperature range of HCFC-141b is 120°–300° C., preferably 150°–240° C. The molar ratio of HF to HCFC-141b can be varied within the range of 3:1 to 15:1 and the preferable ratio is 5:1 to 10:1. The contact time of the reactants and catalyst is in the range of 1 to 60 seconds, preferably 5 to 20 seconds. The fluorination reaction according to the present invention can be performed at atmospheric pressure or at a pressure of not less than 8 atm to allow easy separation of the generated HCl.

The catalyst of the present invention can be used in powder or can be extruded or molded into a pellet depending on the desired form to be used.

In the invention, conversion of HCFC-141b, selectivity of HFC-143a and yield of HFC-143a are defined as follows.

$$\text{Conversion}(\%) \text{ of HCFC-141b} = \frac{\text{HCFC-141b reacted}}{\text{HCFC-141b supplied}} \times 100$$

$$\text{Selectivity}(\%) \text{ of HFC-143a} = \frac{\text{HFC-143a produced}}{\text{HCFC-141b reacted}} \times 100$$

$$\text{Yield}(\%) \text{ of HFC-143a} = \frac{\text{HFC-143a produced}}{\text{HCFC-141b supplied}} \times 100$$

A better understanding of the present invention may be obtained in light of the following examples which are set forth to illustrate, but are not to be construed to limit the present invention.

PREPARATION OF THE CATALYST

EXAMPLE I 558 g of chromic hydroxide ($Cr(OH)_3.H_2O$) and 2030 g of $MgCl_2.6H_2O$ were mixed with 1 L of water to adjust the weight ratio of Cr:Mg to be 1:1, and then 1 L of 48% aqueous solution of HF was added thereto. Then the mixture was reacted at the temperature range of room temperature to 80° C. for 1 hour and the resultant was filtered and dried. The dried catalyst was calcined at 400° C. for 5 hours and formed into a cylindrical pellet (4 mm×4 mm).

EXAMPLES 2–5

Catalysts were prepared according to the same procedure as Example 1, but the weight ratio of Cr and Mg was changed as shown in Table 1 below.

TABLE 1

The composition of the prepared catalyst

| Example No. | Composition of Catalyst (wt. ratio) |
|---|---|
| 2 | Cr:Mg = 1:0.3 |
| 3 | Cr:Mg = 1:4 |
| 4 | Cr:Mg = 1:2 |
| 5 | Cr:Mg = 1:0.5 |

PREPARATION OF HFC-143a 50 g of the pelletized catalyst as prepared in Example 1 was charged into a cylindrical reactor made of Inconel-600 tube (2.54 cm (i.d.)×30 cm (length)) and it was gradually heated to the temperature of 400° C. while supplying nitrogen at a rate of 50 ml/min to dry the catalyst. The reactor was cooled to a temperature of 200° C. and HF and nitrogen were passed through at a rate of 50 ml/min, respectively for 4 hours. Then, the temperature of the reactor was raised gradually and maintained at 400° C. for 30 minutes. The temperature of the reactor was lowered again to 200° C. and HCFC-141b and HF were supplied at a molar ratio of HCFC-141b: HF=1:10 for a contacting time of 10 seconds. HCFC-141b and HF were passed through the preheater (200° C.) and introduced to the reactor. The effluent from the reactor was washed with an aqueous suspension of MgO to remove HF and HCl and dried with $CaCl_2$ and cooled to –60° C. and then collected.

As a result of analyzing the products by gas chromatography using Porapak N column, it was found that the conversion of HCFC-141b was 100% and selectivity of HFC-143a among the reaction products was 99.8%.

EXAMPLES 7–14

The same procedure to produce HFC-143a was carried out as Example 1, using the same catalyst as in Examples 2–5, only varying the reaction temperature, molar ratio of HF to HCFC-141b and contacting time. The reaction conditions and results are shown in Table 2 below:

TABLE 2

Reaction conditions and results of HFC-143a production

| Exam No. | catayst-used | reaction temp (°C.) | HF/141b (molar ratio) | contact time(s) | HCFC-141b conversion | HFC-143a selectivity (%) |
|---|---|---|---|---|---|---|
| 7 | Ex. 2 | 200 | 5 | 30 | 100 | 99.5 |
| 8 | EX. 2 | 160 | 10 | 10 | 99.0 | 99.0 |
| 9 | EX. 3 | 300 | 3 | 60 | 99.8 | 99.2 |
| 10 | EX. 3 | 129 | 15 | 1 | 95.2 | 94.6 |
| 11 | EX. 4 | 180 | 8 | 5 | 99.8 | 97.6 |
| 12 | EX. 4 | 220 | 8 | 15 | 100 | 99.9 |
| 13 | EX. 5 | 240 | 10 | 20 | 100 | 100 |
| 14 | EX. 5 | 150 | 5 | 10 | 98.5 | 98.2 |

TEST FOR THE DURABILITY OF CATALYTIC ACTIVITY

EXAMPLE 15

The durability of the catalytic activity of the present invention was tested by measuring the decrease of its activity after long period use. The result of the HFC -143a production performed according to the process of Example 6 showed that the conversion of HCFC-141b, and selectivity of HFC-143a after 3 months were 99.0% and 98.5%, respectively, and this indicates that the catalyst of the invention can successively maintain its activity.

What is claimed is:

1. A process for preparing 1,1,1-trifluoroethane (HFC-143a), characterized in that HF and 1,1-dichloro-1-fluoroethane are reacted in a molar ratio of 3:1 to 15:1 at a reaction temperature of 120°–300° C. in the presence of a catalyst which is obtained by mixing chromic hydroxide ($Cr(OH)_3.H_2O$) and an aqueous solution of magnesium chloride, reacting such mixture with a solution of HF and then calcining the resulting product.

2. The process according to claim 1, wherein the reaction temperature is 150°–240° C.

3. The process according to claim 1, wherein the molar ratio of HF to 1,1-dichloro-1-fluoroethane is 5:1 to 10:1.

4. The process according to claim 1, wherein a contacting time of the reactant and the catalyst is 1 to 60 seconds.

5. The process according to claim 4, wherein the contacting time is 5 to 20 seconds.

* * * * *